United States Patent [19]

Rink et al.

[11] Patent Number: 4,848,339
[45] Date of Patent: Jul. 18, 1989

[54] LASER HEATED INTRAVASCULAR CAUTERY CAP ASSEMBLY

[75] Inventors: Dan Rink, Oakland; John Rink, San Francisco; Garrett Lee, Piedmont, all of Calif.

[73] Assignee: Xintec Corporation, Oakland, Calif.

[21] Appl. No.: 179,678

[22] Filed: Apr. 11, 1988

Related U.S. Application Data

[63] Continuation-in-part of Ser. No. 19,755, Feb. 27, 1987, which is a continuation-in-part of Ser. No. 650,889, Sep. 17, 1984.

[51] Int. Cl.⁴ .............................................. A61B 17/22
[52] U.S. Cl. .................................... 128/303.1; 128/398
[58] Field of Search ...................... 128/303.1, 395, 397, 128/398

[56] References Cited

U.S. PATENT DOCUMENTS

| | | | |
|---|---|---|---|
| 4,654,024 | 3/1987 | Crittenden et al. | 128/303.1 |
| 4,662,368 | 5/1987 | Hussein et al. | 128/398 |
| 4,760,845 | 8/1988 | Kovalcheck | 128/398 |
| 4,773,413 | 9/1988 | Hussein et al. | 128/398 |

FOREIGN PATENT DOCUMENTS

| | | | |
|---|---|---|---|
| 178464 | 4/1986 | European Pat. Off. | 128/303.1 |
| 8404879 | 12/1984 | World Int. Prop. O. | 128/303.1 |

*Primary Examiner*—Lee S. Cohen
*Assistant Examiner*—David Shay
*Attorney, Agent, or Firm*—Harris Zimmerman; Howard Cohen

[57] ABSTRACT

An improved laser heated intravascular cautery cap construction includes a generally cylindrical outer-sidewall, and a tappered, annular, distal end wall joining the two sidewalls and defining a closed annular space therebetween. A bore extending axially through the inner sidewall is dimentioned to receive in freely sliding fashion an arterial guidewire or other device such as a doppler flow sensor or an optical bundle for viewing. A unitary or multi-segment annular target element is received within the distal portion of the annular space, and is secured to the outer sidewall adjacent to the end wall with a gap defined between the target element and the inner sidewall. A plurality of holes extend through a connector member parallel to the axis of the sidewalls, each hole receiving therethrough one of a plurality of optical fibers extending through the arterial catheter to a laser light source. Each fiber is aimed at one segment or portion of the target element, so that the fibers may be illuminated selectively to heat the respective portion or segment and the adjacent outer sidewall and distal end wall portions. The air gap defined between the target disc segments and the inner sidewall prevents conduction to the inner sidewall. In a further embodiment, the inner sidewall is lined with a sleeve to further limit heating of the arterial guidewire extending therethrough.

25 Claims, 4 Drawing Sheets

FIG_1

FIG_2

FIG_3

FIG_4

FIG_5

FIG_6

FIG_7

FIG_8

FIG_9     FIG_10

FIG_11

FIG_12

FIG_13

FIG_14

FIG_15

LASER HEATED INTRAVASCULAR CAUTERY CAP ASSEMBLY

REFERENCE TO RELATED APPLICATION

This application is a continuation-in-part of U.S. patent application Ser. No. 07/019,755, filed Feb. 27, 1987 by the present inventors John Rink, Dan Rink, and Garrett Lee which application 07/019,755 is a continuation-in-part of application Ser. No. 06/650,889, filed Sept. 17, 1984.

BACKGROUND OF THE INVENTION

In the rapidly evolving field of intravascular treatment of atherosclerotic disease, it has become apparent that removal of atherosclerotic blockages must be carried out without sustaining injury to the arterial wall. Although laser powered devices have been shown to be effective in alleviating atherosclerotic obstructions, the problem of avoiding damage to the arterial wall has not been overcome with a margin of safety appropriate for routine use of these procedures on human beings.

It has been shown in the prior art that laser heated cautery caps are capable of destroying atherosclerotic occlusions while preventing the potential damage associated with the intravascular use of free laser beams. With regard to laser heated cautery cap procedures within the coronary arteries, it is clear that proper guidance of the cap is essential to avoid thermal damage to the arterial wall. Even so, within the narrow confines of the tortuous coronary arteries, contact between the cautery cap and the arterial wall cannot be avoided entirely. Thus it is essential to direct the thermal energy emanating from the laser heated cautery cap toward the atherosclerotic occlusions while protecting the adjacent arterial wall.

The structures disclosed in the copending parent application of the present patent application display the potential for providing both the proper guidance of the laser heated cautery cap and the ability to direct the thermal energy of the cap to the desired target. The present invention comprises significant improvements in the prior inventions. These improvements are direct toward the ultimate goal of removal of atherosclerotic lesions in narrow arterial passages, such as in the coronary arteries, by means of a percutaneous, non-surgical procedure.

SUMMARY OF THE PRESENT INVENTION

The present invention generally comprises an improved laser heated cautery cap construction that is adapted to optimize the guidance and the thermal directional control of the cap. The cautery cap construction includes a generally cylindrical outer sidewall, a concentric inner sidewall, and a tapered, annular, distal end wall joining the two sidewalls and defining a closed annular space therebetween. A bore extending axially through the inner sidewall is dimensioned to receive an arterial guidewire, viewing bundle, doppler flow sensor or the like therethrough in freely sliding fashion. The arterial guidewire, viewing bundle, or sensor may be extremely narrow in diameter, and capable of being directed through atherosclerotically diseased portions of an artery. The larger cautery cap received concentrically and coaxially about the guidewire is thus directed through tortuous arterial passages by the guidewire.

A unitary or multi-segment annular target element is received within the distal portion of the annular space, and is secured to the outer sidewall adjacent to the end wall with a gap defined between the target disc segments and the inner sidewall. The target element or target segments may be welded to the outer sidewall at the junction of the sidewall with the cap end wall, or elsewhere along the sidewall or distal end face of the cap. The air gap defined between the target element or target segments and the inner sidewall prevents thermal conduction to the inner sidewall, and protects the arterial guidewire or other insert from thermal damage. In a further embodiment, the inner sidewall is lined with a sleeve to further limit heating of the arterial guidewire or other device extending therethrough.

The invention also includes a cap connector member having a distal end dimensioned to be receive in the proximal end of the cautery cap between the inner and outer sidewalls and to form a seal therewith. The proximal end of the cap connector is dimensioned to accept the distal end of an arterial catheter in sealing engagement. A plurality of holes extend through the connector member parallel to the axis of the sidewalls, each hole receiving therethrough one of a plurality of optical fibers extending through the arterial catheter to a laser light source. Each fiber is aimed at one segment of the target disc, so that the fibers may be illuminated selectively to heat the respective target segment or portion and the adjacent outer sidewall and distal end wall portions. Thus the thermal energy of the cap may be directed to selected radial portions of the cap, so that, for example, eccentric atherosclerotic lesions may be thermally destroyed by heat directed thereto from the cap, while adjacent arterial wall portions remain relatively cool and undamaged. Likewise, for relatively concentric atherosclerotic lesions, all target disc segments may be heated simultaneously or in rapid succession to heat the entire periphery of the cap to a temperature sufficient to burn a passage through the lesion. Furthermore, the target discs may be heated to a lower temperature by the laser energy to anneal the arterial wall following revascularization by laser angioplasty, balloon angioplasty, and the like.

BRIEF DESCRIPTION OF THE DRAWING

FIG. 9 is a cross-sectional side elevation of a further embodiment of the cautery cap of the present invention, formed over a substrate of sapphire or the like.

DESCRIPTION OF THE PREFERRED EMBODIMENT

The present invention generally comprises an improved design for a laser heated cautery cap, especially intended for use in treatment of atherosclerotic disease of the human arteries. Salient features of the present invention include the ability to guide the cautery cap through tortuous and narrow arterial passages, such as are found in the coronary arteries, and the ability to direct the thermal energy of the cap toward the atherosclerotic lesions and away from the arterial wall.

With regard to FIGS. 1-4, one embodiment of the present invention includes an outer sidewall 11 formed in a closed curved configuration about a central axis, such as a cylinder or the like. An inner sidewall 12 is likewise formed in a closed curved configuration, and is disposed generally coaxially and concentrically with respect to the outer sidewall. The two sidewalls define therebetween an annular space 13. The diameter of the outer sidewall is quite small, on the order of 1.0-2.5 mm, and the diameter of the bore 14 extending axially through the inner sidewall is less than or equal to approximately 1.0 mm. The bore 14 is adapted to receive therethrough an extremely fine arterial guidewire in freely sliding fashion, so that the cautery cap may translate freely along the guidewire.

Figure 1:
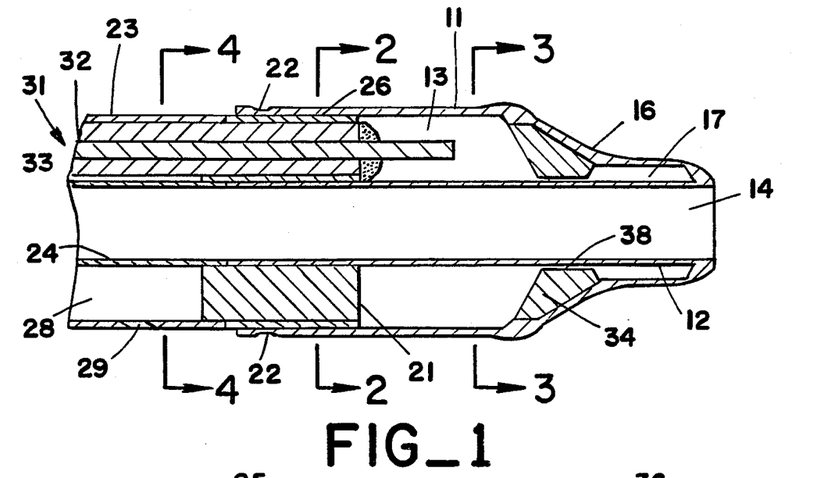
FIG. 1 is a cross-sectional elevation of the improved laser heated cautery cap of the present invention.
Figure 2:
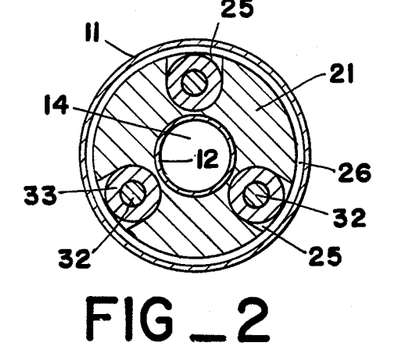
FIG. 2 is a cross-sectional end elevation of the improved laser heated cautery cap of the present invention, taken along line 2—2 of FIG. 1.
Figure 3:
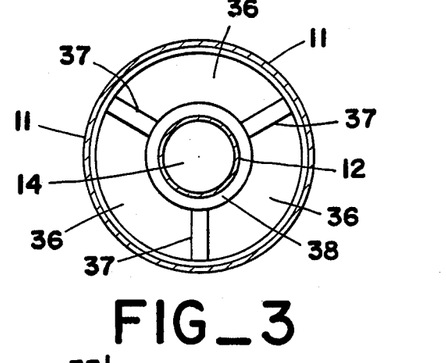
FIG. 3 is a cross-sectional end elevation of the improved laser heated cautery cap of the present invention, taken along line 3—3 of FIG. 1.
Figure 4:
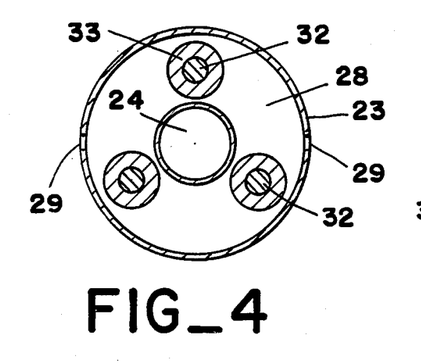
FIG. 4 is a cross-sectional end elevation of the improved laser heated cautery cap of the present invention, taken along line 4—4 of FIG. 1.
Figure 5:
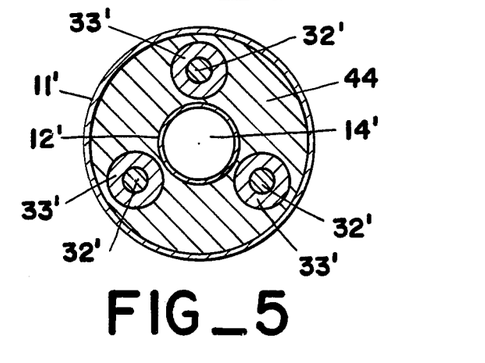
FIG. 5 is a cross-sectional end elevation of the improved laser heated cautery cap of the present invention, taken along line 5—5 of FIG. 6.

The cautery cap is provided with a distal end wall 16 extending continuously between the distal edges of the inner and outer sidewalls 12 and 11 and forming a sealed conjunction therebetween. The end wall 16 tapers distally to form a narrow distal end of the cap far smaller in diameter than the diameter of the outer sidewall 11. The tapered end is a useful aid for advancing the cautery cap through narrow arteries and through narrow passages in atherosclerotically diseased vessels. The taper of the end wall 16 approximates a truncated cone modified by higher-order curvature transitional junctions with the inner and outer sidewalls, defining an annular space 17 which extends continuously with the annular space 13.

Figure 11:
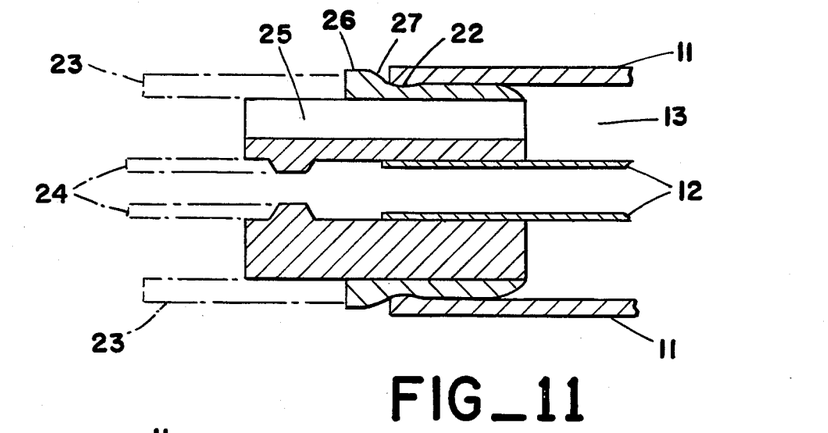
FIG. 11 is a cross-sectional side elevation of the catheter-cap connector member shown in FIG. 2.

At the proximal end of the cautery cap, a catheter-cap connector member 21 is joined to the cap. The connector member 21 comprises a bushing having an inner bore dimensioned to receive therein the inner sidewall 12 in a close tolerance fit, as shown in FIG. 11. The bushing (brass or the like) includes a plurality of channels 25 extending axially in the outer surface thereof, the channels being spaced at equal angles about the axis. An outer ring 26 is dimensioned to be received about the bushing in fixed relationship, the ring serving in part to enclose the channels 25. A reduced diameter annular recess 27 is also provided in the ring 26. The outer sidewall may be crimped into the recess 27, as shown by reference numeral 22, to secure the cap to the connector member. A distal portion of the connector member is thus received in the proximal end of the annular space 13 in sealing engagement, and the proximal end of the connector member is dimensioned to receive and retain the distal end of an outer arterial catheter 23. An inner arterial catheter 24 is secured to the inner surface of the bore of the connector member 21.

A plurality of optical fiber assemblies 31 extend through the space 28 defined between the outer and inner arterial catheters 23 and 24, and pass through the channels 25 in the cap connector 21 into the annular space 13. Adhesive or filler material may be employed to seal the channels 25 and thus seal the inner volume to the cautery cap. The annular space 28 extends the length of the catheter assembly, and may comprise a closed fluid flow channel extending from the exterior of the body to the side of recanalization. The distal end of the outer catheter may be provided with one or more ports 29 for perfusion purposes, so that the side may be flushed and suctioned to eliminate debris caused by the removal of the atherosclerotic plaque. Each optical fiber assembly includes a central optical fiber 32 surrounded by a flexible jacket 33. The optical fibers are spaced generally equally about the axis of the cautery cap, and are directed toward the distal end of the interior of the cap. In the preferred embodiment three optical fibers are shown entering the cap, although the number of optical fibers used depends on available clearances, the side of the fiber assemblies, and the like.

At the distal end of the annular space 13, a segmented target disc 34 is secured to the interior surface of the cap. In the preferred embodiment, the target disc is comprised of three segments 36, each aligned with the axis of one of the optical fibers 32 and disposed to be illuminated thereby. The segments 36 are separated by radially extending gaps 37, so that thermal conduction therebetween is interrupted. Furthermore, each segment 36 is separated from the inner sidewall 12 by an annular air gap 38, so that thermal conduction from the segments 36 to the inner sidewall is also prevented. It may be noted from FIG. 1 that the segments 36 are secured by welding, press fitting, or staking to the inner surface of the distal end wall 16 at the junction of the outer sidewall 11, so that thermal energy generated by the target disc segments is conducted to the respective portions of both the distal end wall and the distal portion of the outer sidewall.

It may be appreciated that although the inner and outer sidewalls and end wall of the cautery cap may be fabricated of surgical stainless steel or the like, for higher power density the target disc may be formed of a refractory material capable of withstanding the extremely high power density (in the range of $10^3$-$10^5$ watts per square centimeter) delivered by the optical fibers from the laser. Therefore in the preferred embodiment the target disc is fashioned of a refractory metal such as titanium, tantalum, or the like which has a very high melting point and relatively high thermal conductivity.

A further embodiment of the laser heated cautery cap of the present invention, depicted in FIG. 6, incorporates some of the components described with reference to the embodiment of FIGS. 1-4, and these components are provided with the same reference numerals modified by a prime (') designation. The cautery cap of FIG. 6 includes an outer sidewall 11', inner sidewall 12', enclosed annular space 13', central bore 14', and distal end wall 16' substantially as described previously. Furthermore, the target disc 34' comprised of segments 36' separated by radial gaps 37' and spaced radially from the inner sidewall 12' by an air gap 38' is also substantially as described in the previous embodiment.

Figure 6:
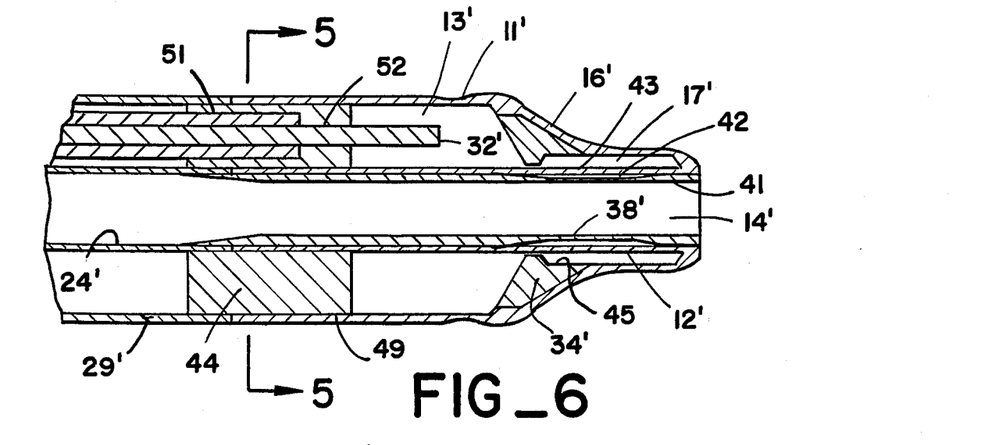
FIG. 6 is a cross-section side elevation of a further embodiment of the improved laser heated cautery cap of the present invention.

A significant feature of the cautery cap of FIG. 6 is the provision of a sleeve 41 dimensioned to be received within the bore 14 in close fit and extending from the distal end of the cap proximally beyond the conjunction with the inner catheter 24'. The sleeve 41 may be formed of stainless steel or the like, and may be welded or otherwise permanently adhered to the inner sidewall. The sleeve includes a shallow annular depression in the outer periphery thereof which defines an annular gap 42 between the sleeve 41 and the inner sidewall. The gap 42 may be filled with a thermally insulating filler, such as ceramic material, air, or other insulating substances. The gap 42 is disposed in confronting alignment with the target disc 34', and is provided to further insulate the inner bore 14' from the thermal energy generated by the target disc. The sleeve 41 and the gap 42 act to protect the arterial guidewire within the bore 14' from damage due to overheating by the high temperatures generated by the target disc.

To further enhance the insulation of the inner sidewall from the high temperature of the target disc, the inner surface portion 43 of the inner sidewall may be plated or otherwise coated with a highly reflective material, such as silver or gold, to limit radiation of thermal energy from the disc to the inner sidewall. The transmission of thermal energy to the inner sidewall is further reduced by providing a counterbore 45 in the target disc, so that the major portion of the target disc is spaced farther apart from the inner sidewall. The reflective plating, the insulating gap 42, and the sleeve 41 are all significant, in that they protect any device which is extended through the bore 14' during laser heating of the cap. For example, recent developments in guidewire technology include the use of plastic coatings and fibers, and other devices such as doppler flow sensors, that must be protected from the high temperatures generated by the target disc.

Figure 8:
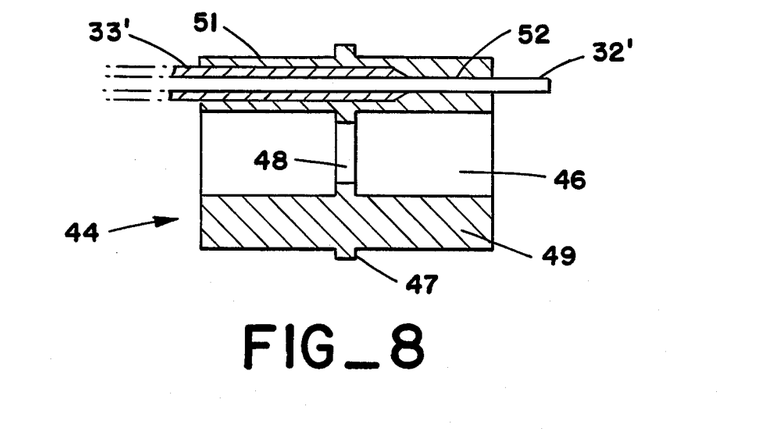
FIG. 8 is a cross-sectional side elevation of the catheter-cap connector member of the present invention.

A further feature of the cautery cap of FIG. 6 lies in the manner of connecting the cap to the outer and inner arterial catheters 23' and 24', respectively. As shown in FIG. 8, this embodiment includes a one piece cathetercap connector member 44. The connector member 44 is generally cylindrical, and includes a bore 46 extending axially therethrough. An annular flange 47 extends radially outwardly from a medial portion of the connector member, and an annular flange 48 extends radially inwardly in the bore 46, both flanges extending generally parallel in radial alignment.

The bore 46 defines a sidewall 49 that is dimensioned to be received between the inner and outer sidewalls of the cautery cap in close fit, sealing engagement, the flanges 47 and 48 abutting the outer and inner sidewalls, respectively, of the cap. The outer proximal peripheral surface of the connector member 44 is dimensioned to receive the outer arterial catheter 23' in permanent engagement, and the inner bore 46 is likewise dimensioned to engage the inner catheter 24'. Adhesives may be used to reinforce the conjunction with the arterial catheters.

The connector member is provided with a plurality of passages 51 extending through the sidewall 49 parallel to the axis of the member 44 and the cautery cap itself. Each passage 51 has a diameter sufficient to receive the jacket 33' of an optical fiber assembly in close tolerance fit. Each passage 51 includes a tapered distal portion 52 having a diameter sufficient to receive only the optical fiber 32' in close tolerance fit. This engagement of the optical fiber determines that the optical fiber assembly forms a seal with the connector member 44 as it passes therethrough. Furthermore, the connector member also seals the proximal end of the annular space 16', so that the cap interior is completely enclosed and impervious to external substances, liquids, and like. The passages 51 are aligned with the segments 36' of the target disc 34', so that each optical fiber 32' directs light energy to its respective target segment to heat the segment and the adjacent outer sidewall and distal end wall portions.

Figure 7:
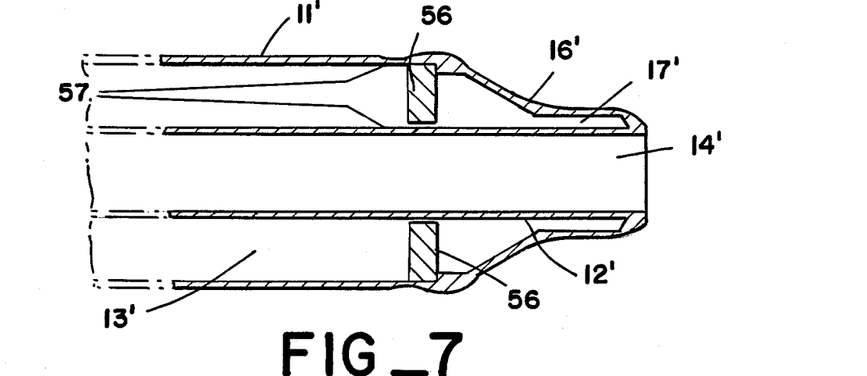
FIG. 7 is a fragmentary cross-sectional side elevation of another embodiment of the improved laser heated cautery cap of the present invention.

In another embodiment of the present invention, shown in FIG. 7, the sidewalls, end wall, and cathetercap connection are substantially as described with reference to either of the previous embodiments. In this embodiment, an annular target disc 56 is modified in its placement within the cap space 16' by spacing the target disc proximally from the distal end wall 16'. Furthermore, the target disc 56 not segmented, and is secured by welding, press fitting, or staking to the outer sidewall 11', so that all conduction of thermal energy developed in the target disc is directed to a continuous annular portion of the outer sidewall of the cautery cap. This feature is useful in annealing an arterial wall that has undergone recanalization procedures such as laser angioplasty, balloon angioplasty, or laser heated cautery cap revascularization with other forms of the present invention. As described previously, the target disc receives laser energy through the optical fibers 32' (not shown in FIG. 7), although the energy density is generally lower for annealing procedures than for recanalization. However, the embodiment of FIG. 7 may be used to soften atherosclerotic lesions that do not severely occlude the arterial lumen, so that mere passage of the cautery cap of FIG. 7 through the diseased artery will reopen the lumen and restore substantially full blood circulation therethrough. The confronting interior surfaces 57 of the inner and outer sidewalls may be plated with a highly reflective material, such as gold, to reduce the radiant transmission of thermal energy from the target to the sidewalls.

Figure 12:
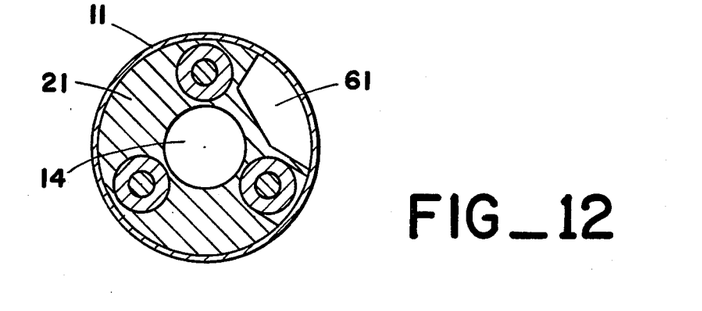
FIG. 12 is a cross-sectional side elevation of a further embodiment of the catheter-cap connector member, including a radio-opaque angular position marker.
Figure 13:
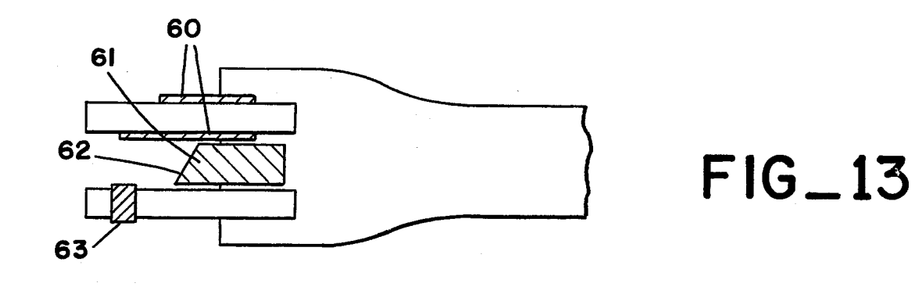
FIG. 13 is a side elevation silhouette view of the appearance of the radio-opaque marker shown in FIG. 12.

To make full use of the vectored thermal energy delivered by the cautery cap of the present invention, it is necessary for the surgeon to be apprised of the rotational orientation of the cap prior to heating through the optical fiber or fibers. With regard to FIGS. 12 and 13, the connector member 21 may be provided with an orientation marker 61, comprising a tab extending proximally from the proximal end surface of the connector member. The tab subtends an angle about the axis of the cap that is less than the angular spacing of the channels that receive the optical fibers, so that the tab demarcates a location between two selected optical fibers. The tab is formed of a radio-opaque material, such as gold or other suitable materials known in the prior art, resulting in a telltale appearance in fluoroscopic or x-ray images, as shown in FIG. 13. It should be noted that the proximal edge 62 of the tab is formed at an oblique angle, so that a full profile image of the tab may be resolved as either a 0° or 180° orientation. Alternatively, or in addition, a selected one of the optical fibers may be provided with a gold band 63 secured thereto adjacent to the cap conjunction, so that the optical fibers may be identified and their orientation determined during recanalization procedures. As a further alternative, a pair of radio-opaque wires 60 of differential length may be provided adjacent to an optical fiber extending from the cautery cap, so that the rotational angle of the cap may be observed through x-ray means.

Figure 9:
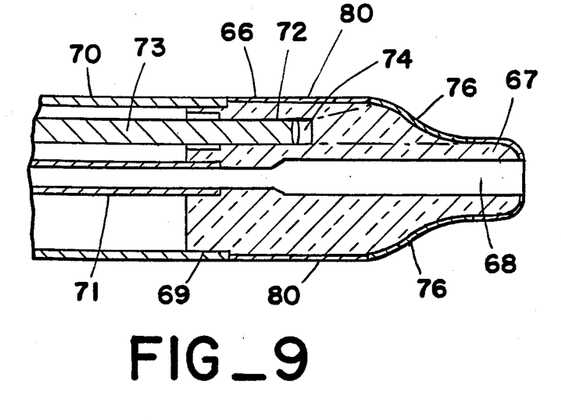
Figure 10:
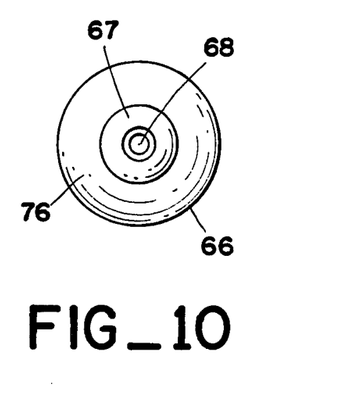
FIG. 10 is an end view of the cautery cap embodiment shown in FIG. 9.

A further embodiment of the improved cautery cap of the present invention, shown in FIGS. 9 and 10, functions similarly to the embodiments described above but features a construction which differs in several important aspects. The cautery cap includes a generally cylindrical body portion 66 and an integral tapered distal end 67 having an outer configuration similar to the previous embodiments. However, in this embodiment the portions 66 and 67 are formed of a solid crystalline substance, such as sapphire, which is not only very transparent, but also refractory by virtue of its extremely high melting point and high strength at high temperatures. A central bore 68 extends axially through the cap, formed by drilling or the like. The proximal end of the body portion 66 is provided with a reduced diameter annulus 69 to receive and retain the end of an outer catheter 70, and the proximal end of the bore 68 is counterbored to secure the end of an inner catheter 71. As before, the annular space between the two catheters may be used as a fluid conduit for perfusion and vacuum aspiration purposes.

A plurality of holes 72 are drilled or bored into the proximal end of the body portion 66, extending parallel to the axis thereof, and spaced at equal angles about the axis. Each hole 72 is dimensioned to receive the distal end of an optical fiber 73, to deliver laser light energy therethrough to the cap. At the distal end of each hole 72, there is a small closed space 74 which may be filled with transparent gas, or a fluid having an index of refraction which optimizes the transfer of laser energy into the crystalline structure.

The sapphire or similar crystalline material is used as a highly transparent, light conductive substrate upon which an outer cautery cap structure may be formed. Thus, a salient feature of this embodiment is the provision of a layer 76 of material such as tantalum or the like of high absorptivity, low reactivity, high thermal conductivity, and high melting point. The layer 76 may be formed by plating, dipping, chemical vapor deposition, metallorganic vapor deposition, mechanical keying, or the like. The layer 76 extends at least about the tapered surface area of the body portion 66 and distal end 67, to intercept the laser energy from the optical fibers 73 and convert it to thermal energy. The layer 76 may be divided, by resist pattern techniques used in integrated circuit fabrication, so that each optical fiber acts to heat a well-defined angular portion of the cap distal end. To this end, the distal ends of the optical fibers 73 may be shaped to direct the light energy emanating therefrom toward the target comprising the layer 76.

Furthermore, the outer surface of the cap of FIG. 9 not covered by the layer 76 is provided with a layer 80 of material such as gold, gold alloy, or the like that is highly reflective, with low reactivity and high melting point. The layer 80 acts to retain all the laser illumination within the cautery cap, so that there is no accidental free laser beam impinging on the surrounding tissue. The layer 80 may be extended to cover substantially the entire outer surface of the cap, and the surface of the central bore, so that the guidewire or other device extending through the bore is protected from thermal destruction and virtually all the laser energy delivered to the cap is contained therein and converted to thermal energy. A material such as gold forming the layer 80 may be further protected by an outer layer of hard, non-reactive material, such as titanium nitride. The outer layer or layers 80 may be extended to cover the target layer portions 76, so that manufacturing is simplified and the outer appearance is uniform.

The cap construction shown in FIGS. 9 and 10 exhibits the advantages of unitary construction, so that fabrication is simplified and reliability is increased by reducing the opportunity for components to fail. Also, a material such as sapphire has a great tolerance for high temperatures, maintaining its strength and low reactivity, even at high temperatures. The use of sapphire as a substrate on which to deposit the thin layers 76 and 80 permits the formation of a cautery cap having a very low effective thermal mass and thermal conductivity path which more precisely directs the thermal energy to the atherosclerotic lesion to be treated.

As has been noted previously, the cautery cap of the present invention is designed to be used in conjunction with a very small diameter arterial guide wire, which is first advanced through the artery to be treated by percutaneous entrance into the body. The cautery cap is then advanced concentrically and coaxially along the arterial guidewire, using the inner and outer catheters 23 and 24 and the optical fibers themselves to push the assembly slidably along the guidewire. When the cap is correctly placed in impingement with an atherosclerotic lesion to be treated and removed, as determined by concurrent fluoroscopic data, a laser device is actuated to deliver continuous power or a series of pulses to the appropriate target disc segments to heat the portions of the outer sidewall which impinge on the atherosclerotic lesion. An appropriate laser for this purpose is disclosed in copending United States patent application Ser. No. 265,565, filed on 11-1-88 by John Rink. A device for selectively delivering the laser energy to the appropriate optical fibers and switching among the optical fibers is disclosed in copending United States patent application Ser. No. 180,950, filed on 4-11-88 by Rink et al.

It may be appreciated that the laser energy may be delivered to all target segments 36 or 36' to heat the entire periphery of the distal portion of the cautery cap, to either "tunnel" through an atherosclerotic occlusion, with high temperatures sufficient to destroy the occlusion, or to perform a "thermal angioplasty" with warm temperatures sufficient to soften the occlusion and permit the cautery cap to be pushed therethrough. The technique employed depends on the composition of the atherosclerotic plaque and its form and disposition. These latter factors may be examined visually by removal of the central arterial guidewire (after the cautery cap and its associated catheters are advanced to the cite of the lesion), and replacement of the guidewire by an fiberoptic viewing device having a diameter sufficiently small to be passed through the inner catheter 24 or 24' or 71 and through the bore 14 or 14' or 68 to examine the atherosclerotic lesion directly. Likewise, after any of the recanalization procedures described above, the viewing device may be employed to examine the results, and determine further procedures. In addition to or in conjunction with the ports 29, the axial passage extending through the catheter and cap may also be used to flush and aspirate any debris created by the revascularization procedures, and also to inject radio-opaque contrast medium to enhance the data available from fluoroscopic examination.

Figures 14, 15:
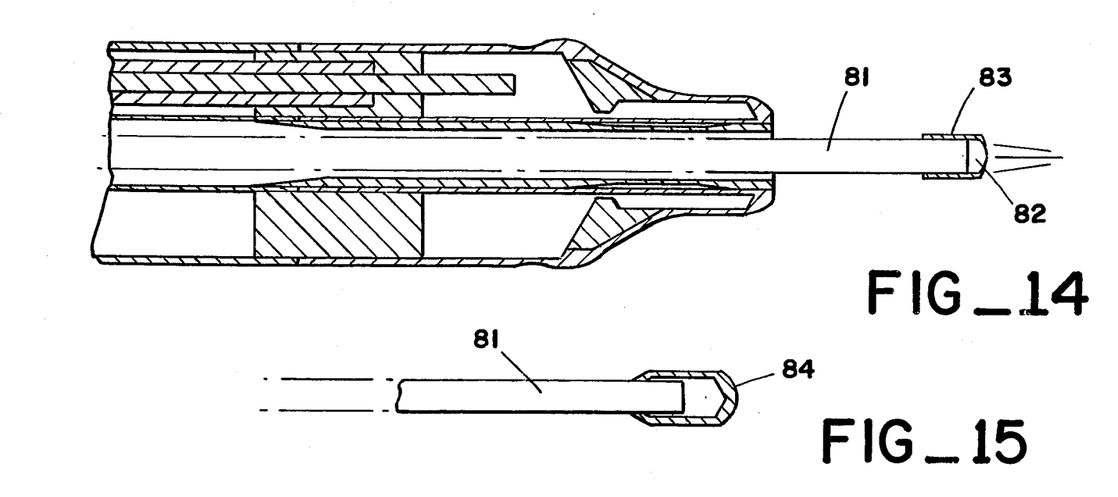
FIG. 14 is a cross-sectional side elevation of a further embodiment, in which an optical fiber capable of transmitting a laser beam is extended through the central opening of the cautery cap.
FIG. 15 is a side view of a further embodiment of the invention of FIG. 14, in which the central free beam optical fiber is replaced with an optical fiber having a micro-cautery cap secured thereto.

The bore extending through the cautery cap embodiments of the present invention may also be used to introduce a further optical fiber 81 through the catheter assembly and cap to the site of an atherosclerotic lesion, as shown in FIG. 14. The optical fiber 81 is provided with a lens 82 at the distal end thereof, the lens comprising either an integral lens or a separate lens of sapphire or the like fused to the distal end of the fiber. A metal jacket of stainless steel or the like is secured about the distal end to protect and retain the lens. The optical fiber emits a free laser beam directed and focused at an atherosclerotic lesion. Alternatively, as shown in FIG. 15, the distal end of the optical fiber 81 may be provided with a diminutive cautery cap 84, which is heated by laser energy transmitted through the optical fiber, as explained with regard to the embodiments described above.

In either of the embodiments of FIGS. 14 or 15, the optical fiber 81 may be inserted into the artery undergoing treatment after the initial arterial guidewire is removed. The fiber with the diminutive cautery cap or free beam lens may be advanced prior to or simultaneously with the coaxial cautery cap, and employed to create or enlarge an initial lumen sufficiently for the larger cautery cap to be translated farther through the vessel. It can also be withdrawn at any time to permit perfusion or aspiration, or insertion of a guidewire.

What is claimed is:

1. An improved intravascular cautery cap construction, including a closed curved outer sidewall extending symmetrically about an axis, an inner sidewall extending concentrically with said outer sidewall and coaxially therewith, a distal end wall joining like distal ends of said sidewalls to form an annular space therebetween, said inner sidewall having an open bore extending axially therethrough, cap connector means secured to like proximal ends of said sidewalls in sealing fashion to enclose said annular space, means for extending a plurality of optical fibers through said cap connector means into said annular space, said optical fibers including distal ends extending parallel to said axis and directed toward said distal end wall, an annular target disc disposed within said annular space and secured to said outer sidewall in axially spaced relationship to said distal end wall, said target disc disposed to be illuminated by said optical fibers and to be heated thereby.

2. An improved intravascular cautery cap construction, including a closed curved outer sidewall extending symmetrically about an axis, an inner sidewall extending concentrically with said outer sidewall and coaxially therewith, a distal end wall joining like distal ends of said sidewalls to form an annular space therebetween, said inner sidewall having an inner surface defining an open bore extending axially therethrough, cap connector means secured to like proximal ends of said sidewalls in sealing fashion to enclose said annular space, means for extending a plurality of optical fibers through said cap connector means into said annular space, said optical fibers including distal ends extending parallel to said axis and directed toward said distal end wall, and an annular target disc disposed within said annular space and impinging on at least one of said outer sidewall or said distal end wall.

3. The improved intravascular cautery cap construction of claim 2, wherein said target disc comprises a plurality of segments separated by a plurality of radially extending gaps, each of said segments disposed to be illuminated by a respective one of said optical fibers and to be heated thereby.

4. The improved intravascular cautery cap construction of claim 2, wherein said distal end wall extends in tapering, narrowing fashion from the distal end of said outer sidewall to the distal end of said inner sidewall.

5. The improved intravascular cautery cap construction of claim 2, wherein said target disc includes an inner peripheral edge extending about said inner sidewall and spaced radially therefrom to prevent thermal conduction therebetween.

6. The improved intravascular cautery cap construction of claim 2, wherein said target disc is secured to said outer sidewall for direct thermal conduction thereto.

7. The improved intravascular cautery cap construction of claim 2, wherein said target disc is secured to said distal end wall for direct thermal conduction thereto.

8. The improved intravascular cautery cap construction of claim 2, wherein said cap connector means includes a connector member having a continuously curved outer surface, a plurality of channels extending in said outer surface parallel to said axis, each of said channels receiving one of said optical fibers extending therein, and a connector bore extending therethrough and aligned along said axis, said inner sidewall received in said connector bore in close tolerance fit.

9. The improved intravascular cautery cap construction of claim 8, wherein said cap connector means further includes a sleeve member received about said connector member in close tolerance fit and to retain said optical fibers in said channels.

10. The improved intravascular cautery cap construction of claim 9, wherein said sleeve member includes an outer surface configuration received within the proximal end of said outer sidewall in close tolerance fit.

11. The improved intravascular cautery cap construction of claim 2, further including an insulating sleeve disposed concentrically within said bore in said inner sidewall and extending from the proximal end to the distal end of said inner sidewall.

12. The improved intravascular cautery cap construction of claim 11, wherein said insulating sleeve includes a distal portion spaced apart radially from said inner sidewall to define an annular insulating gap between an inner surface of said insulating sleeve and said inner sidewall, said insulating gap being generally disposed in registration with said target disc.

13. The improved intravascular cautery cap construction of claim 12, further including a high reflectivity surface coating secured to the inner surface of said insulating sleeve.

14. The improved intravascular cautery cap construction of claim 2, further including a high reflectivity surface coating secured to the inner surface of said inner sidewall and the inner surface of said outer sidewall.

15. The improved intravascular cautery cap construction of claim 2, further including a central optical fiber extending through said open bore of said inner sidewall, said central optical fiber adapted to be connected to a laser light source and disposed to direct the laser light distally and centrally from said cautery cap bore.

16. The improved intravascular cautery cap construction of claim 2, further including a central optical fiber extending through said open bore of said inner sidewall, said central optical fiber adapted to be connected to a laser light source, a diminutive cautery cap secured to a distal end of said central optical fiber and adapted to be heated selectively by the laser light.

17. An improved intravascular cautery cap construction, including a solid body member formed of a transparent, high temperature material, said body member being substantially cylindrical and including a tapered distal end, a central bore extending axially through said body member and through said tapered distal end, a plurality of holes extending in a proximal end surface of said body member and disposed parallel to an axis thereof, each of said plurality of holes receiving one of a plurality of optical fibers therein, said optical fibers being adapted to be connected to a selectively controlled laser light source and disposed to transmit the laser light into said body member, and first surface coating means secured to outer surface portions of said body member to receive and absorb the laser light illumination and generate thermal energy therefrom.

18. The improved intravascular cautery cap construction of claim 17, wherein said first surface coating means includes a surface coating applied to said tapered distal end of said body member.

19. The improved intravascular cautery cap construction of claim 17, further including second, reflective surface coating means applied to substantially the entire outer surface of said body member to retain the laser light therein.

20. The improved intravascular cautery cap construction of claim 19, wherein said second surface coating means includes a surface coating applied additionally to the surface of the body member defining said central bore to reduce thermal conduction to any device disposed in said central bore.

21. The improved intravascular cautery cap construction of claim 19, further including third surface coating means of hard, reflective material, said third surface coating means extending over at least said second surface coating means to protect said second surface coating means.

22. The improved intravascular cautery cap construction of claim 17, further including a central optical fiber dimensioned to be extended through said open bore of said inner sidewall, said central optical fiber adapted to be connected to a laser light source and disposed to direct the laser light distally and centrally from said cautery cap bore.

23. The improved intravascular cautery cap construction of claim 17, further including a central optical fiber dimensioned to be extended through said open bore, said central optical fiber adapted to be connected to a laser light source, a diminutive cautery cap secured to the distal end of said central optical fiber and adapted to be heated selectively by the laser light.

24. A method for removal of atherosclerotic lesions in arterial vessels, including the steps of advancing an arterial guidewire through an artery to an atherosclerotic lesion, providing a laser heated cautery cap with a bore extending axially therethrough and a plurality of optical fibers connected at the cautery cap in an annular array to deliver laser light energy selectively to the cautery cap, advancing the cautery cap coaxially about and distally along the arterial guidewire to impinge on the atherosclerotic lesion, delivering laser light energy through the optical fibers to the interior of the cautery cap to heat the cautery cap and destroy the atherosclerotic lesion in contact therewith.

25. The method of claim 24, further including providing a plurality of target segments within the cautery cap, each disposed to receive laser light energy from one of said plurality of optical fibers, each target segment being secured to a respective peripheral portion of the cautery cap and disposed to deliver thermal energy thereto in response to illumination by the respective optical fiber.

* * * * *